United States Patent
Lewis et al.

[11] Patent Number: 6,020,580
[45] Date of Patent: *Feb. 1, 2000

[54] MICROWAVE APPLICATOR HAVING A MECHANICAL MEANS FOR TUNING

[75] Inventors: David Andrew Lewis, Carmel; Stanley Joseph Whitehair, Peekskill, both of N.Y.; Alfred Viehbeck, Austin, Tex.; Martin Yonnone, Fairfield, Conn.; William V. Corso, Ronkonkoma, N.Y.; Bernard Krieger, Stamford, Conn.

[73] Assignee: International Business Machines Corporation, Armonk, N.Y.

[*] Notice: This patent is subject to a terminal disclaimer.

[21] Appl. No.: 09/003,016

[22] Filed: Jan. 5, 1998

Related U.S. Application Data

[60] Provisional application No. 60/034,718, Jan. 6, 1997.

[51] Int. Cl.$^7$ .................................................... H05B 6/70
[52] U.S. Cl. .......................... 219/696; 219/690; 219/745; 219/698; 219/750
[58] Field of Search .................................... 219/690, 691, 219/693, 696, 698, 695, 678, 679, 699, 670, 745, 746, 750, 752

[56] References Cited

U.S. PATENT DOCUMENTS

| | | |
|---|---|---|
| 3,461,261 | 8/1969 | Lewis et al. . |
| 3,739,130 | 6/1973 | White .................................... 219/690 |
| 4,507,588 | 3/1985 | Asmussen et al. . |
| 4,585,668 | 4/1986 | Asmussen et al. . |
| 4,630,566 | 12/1986 | Asmussen et al. . |
| 4,727,293 | 2/1988 | Asmussen et al. . |
| 4,777,336 | 10/1988 | Asmussen et al. . |
| 4,792,772 | 12/1988 | Asmussen et al. . |
| 5,241,040 | 8/1993 | Cuomo et al. ........................ 528/353 |
| 5,250,773 | 10/1993 | Lind et al. ............................ 219/696 |
| 5,471,037 | 11/1995 | Goethal et al. . |
| 5,837,978 | 11/1998 | Hatzakis, Jr. et al. ................ 219/702 |
| 5,869,817 | 2/1999 | Zietlow et al. ....................... 219/696 |

Primary Examiner—Tu Ba Hoang
Attorney, Agent, or Firm—Ohlandt, Greeley, Ruggiero & Perle

[57] ABSTRACT

A microwave applicator includes an elongated chamber, preferably having a cylindrical shape, for processing materials therein. A waveguide, connected to the elongated chamber, couples microwave power into the elongated chamber. The cross-sectional area of the elongated chamber can be mechanically adjusted to control and maintain the microwave field uniformity and resonant mode, preferably the length independent mode $TM_{010}$, during the processing of the material. The applicator can thus provide microwave energy having a substantially uniform field distribution over a large area for processing materials, for example, a web or sheet like product, plywood and pre-impregnated cloth, in a continuous manner.

20 Claims, 5 Drawing Sheets

MICROWAVE APPLICATOR HAVING A MECHANICAL MEANS FOR TUNING

This application claims the priority from U.S. Provisional Application Ser. No. 60/034,718 filed Jan. 6, 1997.

FIELD OF INVENTION

The present invention is related to microwave applicators and, more particularly, to a mechanical means for tuning a microwave applicator to provide a uniform electric field.

BACKGROUND OF THE INVENTION

Microwave radiation can be applied to a material in a number of ways, using single mode, multimode applicators, traveling wave applicators, slow wave applicators, fringing field applicators and through free space. Each of the aforementioned methods of coupling microwave energy into a material has its advantages and disadvantages which usually depend on the dielectric properties, size and shape, of the materials to be processed and the type of processing (batch, continuous, . . . etc.) to be performed.

Efficient microwave energy transfer is a function of many variables as processing occurs. A number of these variables are material related, e.g., the material type and density and material temperature as well as the time history of both the material temperature and the applied electric field.

Other factors that influence coupling are related to the applicator, material geometry and size and the frequency or wavelength of the electromagnetic energy. Electromagnetic coupling depends on applicator size and geometry, material size and shape, the position of the material within the applicator, and even the relative sizes and shapes of the material and the applicator. In addition, both the applicator and material dimensions may change during heating which further complicates the efficient transfer of energy to the material.

Accordingly, a problem arises when attempting to generate a uniform microwave field across a relatively large surface for different material loads. As generally understood, if the volume of an applicator becomes too large, more than one electric field pattern can co-exist in the applicator, thereby making it multimode and introducing electric field non-uniformities. Current microwave applicators are incapable of generating a uniform microwave field across a surface that is relatively large compared to the wavelength of the radiation.

For instance, traveling wave applicators have some potential for providing uniformity. However, stray reflections, such as those that occur at the edges of a workpiece or any non-uniformity in the structure of the applicator can create standing waves leading to thermal non-uniformities. This is especially problematic in cases in which the material travels through more than one applicator and the dielectric properties of the material change depending on the processing conditions in the previous applicator.

An applicator design which shows some promise for applying uniform fields is a single mode applicator, provided that the fields can be extended over a sufficiently large region. This type of applicator can be tuned to specific electric field patterns (resonance modes) by varying the volume of the applicator.

One such approach is found in U.S. Pat. Nos. 4,507,588, 4,585,668, 4,630,566, 4,727,293, and U.S. Pat. No. 4,792,772 (Asmussen) all of which disclose methods and apparatuses in which a single mode resonant microwave applicator can be critically coupled by varying two separate, almost orthogonal variables, specifically the cavity length (by moving a short circuit) and the antenna position.

The Asmussen devices include a variable penetration antenna structure which acts to launch radiation into the applicator. The main advantage of the Asmussen device is that it enables complete critical coupling over a wide range of impedances (generated by the load in the applicator) and without the use of any external coupling structure. Critical coupling can thus be achieved by moving the short and the antenna appropriately.

By moving the flat part of the cavity wall (in a cylinder) in the z-direction (e.g., along the centerline of the cylinder), a wide range of electromagnetic modes can be established and maintained, even as the load varies (due to processing, e.g., temperature changing, material curing, etc.) However, one series of modes that can not be routinely excited are length independent modes, $TM_{xy0}$ and $TE_{xy0}$. The resonant frequency of these modes are only dependent on the diameter of the loaded structure. As a result, if the load changes during processing (e.g., the dielectric properties change, due to increased temperature, curing, phase change in the material and so forth), the resonant frequency in the cavity changes from an initial, fixed processing frequency, usually 2450 MHz or 915 MHz (which are the ISM bands allowed by the Federal Communication Commission (FCC)). The Asmussen devices are thus not capable of maintaining certain modes in a controlled manner, namely the length independent modes ($TM_{xy0}$) because these modes are dependent on the diameter of the applicator only.

U.S. Pat. No. 5,471,037 (Goethal) discloses a single mode cylindrical applicator that operates in the $TM_{02n}$ resonant mode. The microwave applicator is designed to process monomers in order to produce prepolymers. The size of the microwave applicator is selected according to the particular monomers being processed (i.e., fixed dimension applicator). Therefore, there is no mechanism for altering the diameter of the applicator to account for substantially different loads or substantially different dielectric properties.

U.S. Pat. No. 3,461,261 (Lewis) relates to a $TM_{02n}$ applicator that processes threads and yarns with the workpieces passing along the central axis of the applicator. The dimensions of the microwave applicator are selected according to the materials being processed (i.e., fixed dimension applicator).

In general, to process wide objects in a continuous manner, such as a web or sheet like product, as found in the paper industry, lumber industry (plywood) or electronics industry (in pre-impregnated cloth for circuit board manufacture), it is desirable to be able to (i) provide a uniform electric field over the entire product for uniform heating; (ii) vary the applicator to allow for variations in the dielectric properties of a continuously moving workpiece and, thus, vary the coupling of the radiation to the product; and (iii) control the microwave power reaching the product to control the temperature-time profile of the web.

Figure 1:
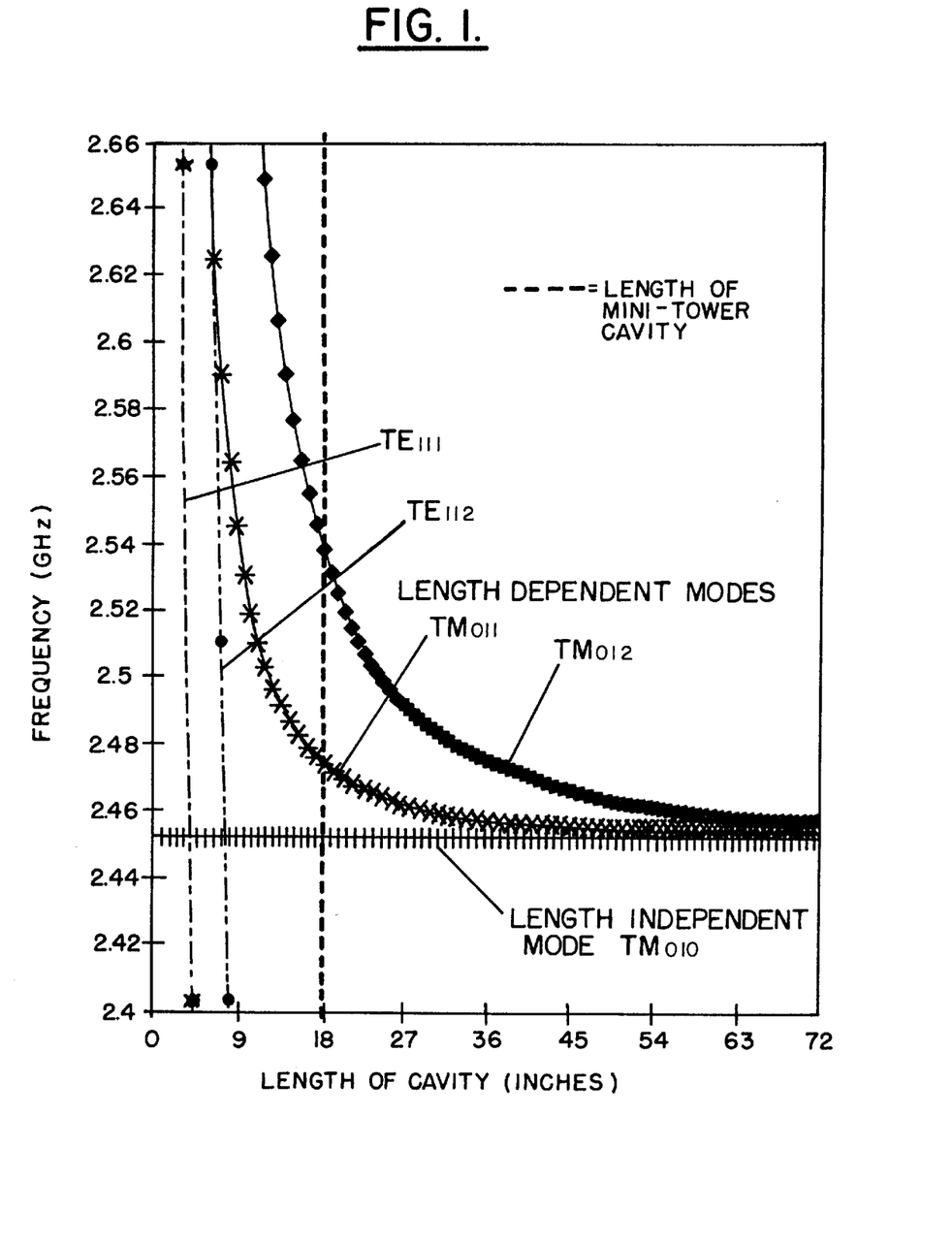
FIG. 1 illustrates a variation of resonant frequencies of different modes versus cavity length of a microwave applicator, having a cavity diameter of 3.85 inches.

The electric field pattern sustained by the $TM_{oyo}$ series of modes, where y=1, 2 or greater, is oriented along the z-axis of the applicator and is of constant intensity along the entire length of the applicator for an empty cavity. This is an ideal mode for the processing of a web-like material. Referring to FIG. 1 (a mode chart), it can be seen that the $TM_{010}$ mode is independent of the cavity length. Therefore, a low loss, infinitely long applicator is capable of sustaining the same electric field intensity throughout the length.

There is currently no method to manipulate the dimensions of the microwave applicator, particularly the cross-sectional diameter, to maintain the resonance and achieve uniform heating of the material (load), using length independent modes. It should also be noted that all electromagnetic modes are dependent on a cross-sectional diameter of the microwave applicator (if the applicator is cylindrical or spheroid), and many have an additional dependence on the length of the applicator.

Accordingly, it is an object of the present invention to provide a microwave applicator capable of having improved energy field distribution over a wide area, as compared to the prior art.

It is also an object of the present invention to provide a microwave applicator wherein the cross-sectional area, i.e., the diameter, of the applicator can be continuously adjusted to maintain the resonance of the applicator over a wide range of dielectric loads and, thus, be able to couple microwave energy into the load.

Another object of the invention is to provide a microwave applicator capable of controlling and maintaining different resonant modes, specifically the length independent modes ($TM_{xy0}$ and $TE_{xy0}$ modes)

It is a further object of the invention to provide an elongated cylindrical microwave applicator having an adjustable cross-sectional dimension.

It is also an object of the invention to provide an elongated cylindrical microwave applicator that allows a uniform electric and magnetic field to be applied to a sheet of material being transported therethrough, in a continuous manner.

It is a further object of the invention to provide an elongated cylindrical microwave applicator that launches radiation at more than one input and provides uniform electric and magnetic fields along its length.

SUMMARY OF THE INVENTION

A microwave applicator includes an elongated chamber, preferably having a cylindrical shape, for processing materials therein. A waveguide, connected to the elongated chamber, couples microwave power into the elongated chamber. The cross-sectional area of the elongated chamber can be mechanically adjusted to control and maintain the microwave field uniformity and resonant mode, preferably a length independent mode $TM_{010}$, during the processing of the material. The applicator thus provides microwave energy having a substantially uniform field distribution over a large area for processing materials, for example, a web in a continuous manner.

It has been discovered, in the case of a cylindrical microwave applicator, that the cross-section of the applicator does not need to be perfectly circular to maintain the Transverse Magnetic (TM) or Transverse Electric (TE) resonant modes. In accordance with the discovery, the present invention provides several embodiments for adjusting the cross-sectional diameter of the applicator.

One embodiment provides an applicator that is separated into two or more parts along its length, preferably into two equal cylindrical halves. A first cylindrical half is fixed to a support structure. A second cylindrical half is mechanically adjustable towards and away from the fixed cylindrical half to increase or decrease the cross-sectional diameter of the applicator.

Another embodiment provides an applicator that has a flexible, metal foil positioned therein, between sidewalls of the applicator and along the length of the applicator such that the metal foil forms one portion of the resonant cavity. The metal foil is formed of a flexible metal whose shape can be easily altered by applying or removing pressure thereon. In this way, the cross-sectional area of the applicator can be altered by adjusting the shape of the metal foil.

DETAILED DESCRIPTION OF THE INVENTION

Figure 2:
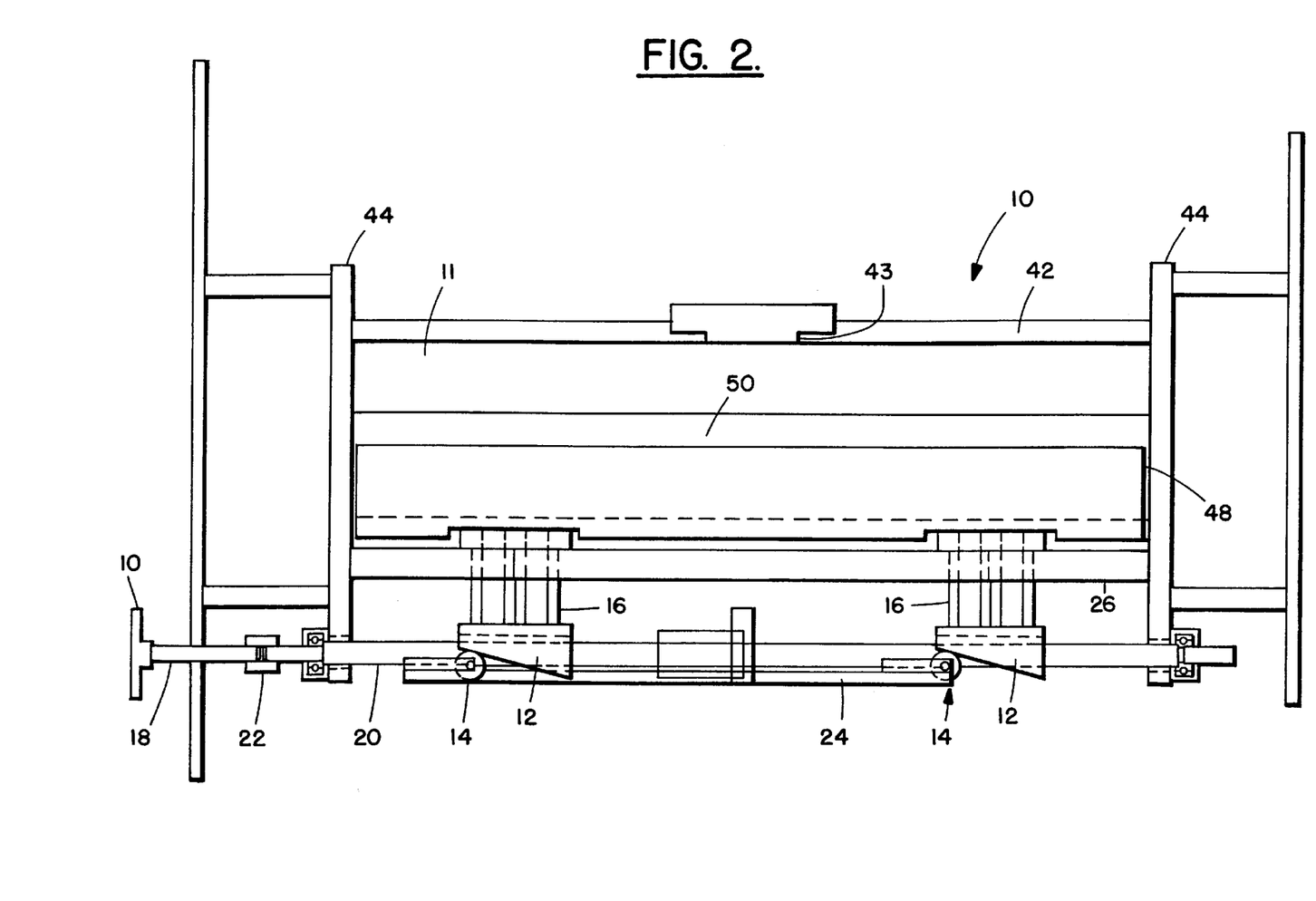
FIG. 2 illustrates a side schematic view of a first embodiment of a microwave applicator constructed in accordance with the present invention.

Referring to FIG. 2, a microwave applicator 10 in accordance with the present invention includes an elongated cylindrical chamber 11 having a resonant cavity therein. A power source is coupled to the resonant cavity preferably through a flange end waveguide extension 43. The energy is launched into cylindrical chamber 11, via waveguide extension 43. Note that, depending on the type of load or processing, the energy can be end launched from one end of the cylinder, side launched through a side wall of the cylinder or multi-launched.

It has been discovered, in the case of a cylindrical microwave applicator, that the cross-section of the cylindrical chamber does not need to be perfectly circular to maintain either a Transverse Magnetic (TM) or Transverse Electric (TE) resonant mode. This is especially the case for the $TM_{010}$ length independent mode. In other modes, such as $TE_{111}$, one mode orientation may become preferred over an infinite number of possible orientations for this mode, as the cross-section becomes grossly different from a circle (approaching an ellipse). This may be both desirable and undesirable, depending on the material to be processed. However, if the cross-sectional deviation is too great, some modes may be suppressed or impossible to obtain, especially modes such as the $TE_{111}$ mode with strong radial fields.

Based on the above principles, it is now possible to design an elongated cylindrical applicator that can maintain the TM and TE resonant modes even though the cross-section of the applicator is not perfectly circular, e.g., an ellipse, oval, square, rectangle and so forth. The applicator can be approximately 20 percent off circular and still maintain a desired resonant mode. In light of these discoveries, the present invention provides an elongated cylindrical microwave applicator that is capable of controlling and maintaining different resonant modes, particularly the length independent modes. Various preferred forms of microwave applicator 10 will be discussed in detail below.

Referring again to FIG. 2, the first embodiment of the invention provides an applicator 10 in which the tuning capability is achieved by separating or slicing an elongated chamber 11, preferably having a cylindrical shape, into two or more parts along the length of chamber 11 (e.g., along its z-axis). These parts can be moved closer together or further apart in a continuous, uniform manner to effectively enlarge the cross-sectional area (e.g., the diameter) of the resonant cavity of the applicator. It has been discovered that the different TM and TE resonant modes can be maintained even though the cross-sectional area of chamber 11 is not perfectly circular, e.g., ellipse, oval, square, rectangle and so forth.

From an electrical perspective, it is preferable to have more than two pieces to maintain more of a circular cross-section. However, from a mechanical perspective, it is desirable to minimize the number of moving pieces. Note while the cylinder may be separated anywhere along the cylinder into two or more parts, it is preferred that elongated cylindrical chamber 11 be separated along the center-line of the cylinder to produce two approximately equal cylindrical halves 42, 48.

The mechanics involved in moving two cylindrical halves 42, 48 of chamber 11 apart in a constant manner while maintaining parallelism is non-trivial. For the pair of cylindrical halves 42, 48 preferably approximately 4 inches in diameter, a movement apart of 0.1 inches results in a change in the resonant frequency of the applicator of 60+/−3 MHz. It is thus important to be able to move the cylinders apart over the diameter range of approximately 3.6 to 4.1 inches in a uniform and controlled manner.

FIG. 2 schematically illustrates one method of moving cylindrical halves 42, 48. A first cylinder half 42 is fixed between two support structures 44; and a second cylinder half 48 floats, e.g., is allowed to slide towards and away from first cylindrical half 42. The movement of second cylinder half 48 is governed by the movement of a threaded rod 20. A knob 10 is connected to a short shaft 18 which is coupled to threaded rod 20, by a collar 22. Threaded rod 20 is also fixedly attached to a plate 24, which has preferably four roller bearings 14 attached thereto. When threaded rod 20 is turned (by rotating knob 10), the rollers travel in one direction or the other. The rollers provide a camming action on inclined planes 12, which are attached to the floating second cylinder half 48, across a spring 16. Accordingly, second cylinder half 48 can be moved towards and away from first cylindrical half 42 by rotating knob 10 in the appropriate direction. The above operation may either be performed manually or in a fully automated fashion through computer control. The second cylinder half 48 is an electrical connection with the supports 44, via flexible conductive materials.

The design of applicator 10 is useful for processing web-like materials. Such materials may be inserted into applicator 10 through a space 50 provided between first and second cylindrical halves 42, 48 (i.e., the web moves orthogonally to the plane of the drawing). As such, the range of motion of second cylindrical half 48 may be limited to provide a desired spacing between first cylindrical half 42 and second cylindrical half 48 depending on the dimensions of the materials to be processed.

However, one problem with this embodiment is that for moderately high microwave powers, there are significant electrical currents generated in the walls of the applicator, up to the skin depth of the radiation in the material, which is of the order of 2 to 5 micrometers for 2.45 GHz radiation in a metallic (e.g., brass) cylinder. If there is a break in the electrical path, there can be arcing in the applicator walls. This results in relatively a low Q factor for the applicator with lower electric field strengths and poorer performance. If the Q is too small (the tuning dip too broad), there may be sufficient overlap between modes that spurious (undesirable) modes will be supported simultaneously, resulting in a multimode applicator with poor uniformity control or by not being able to support the desired mode.

Figure 3A:
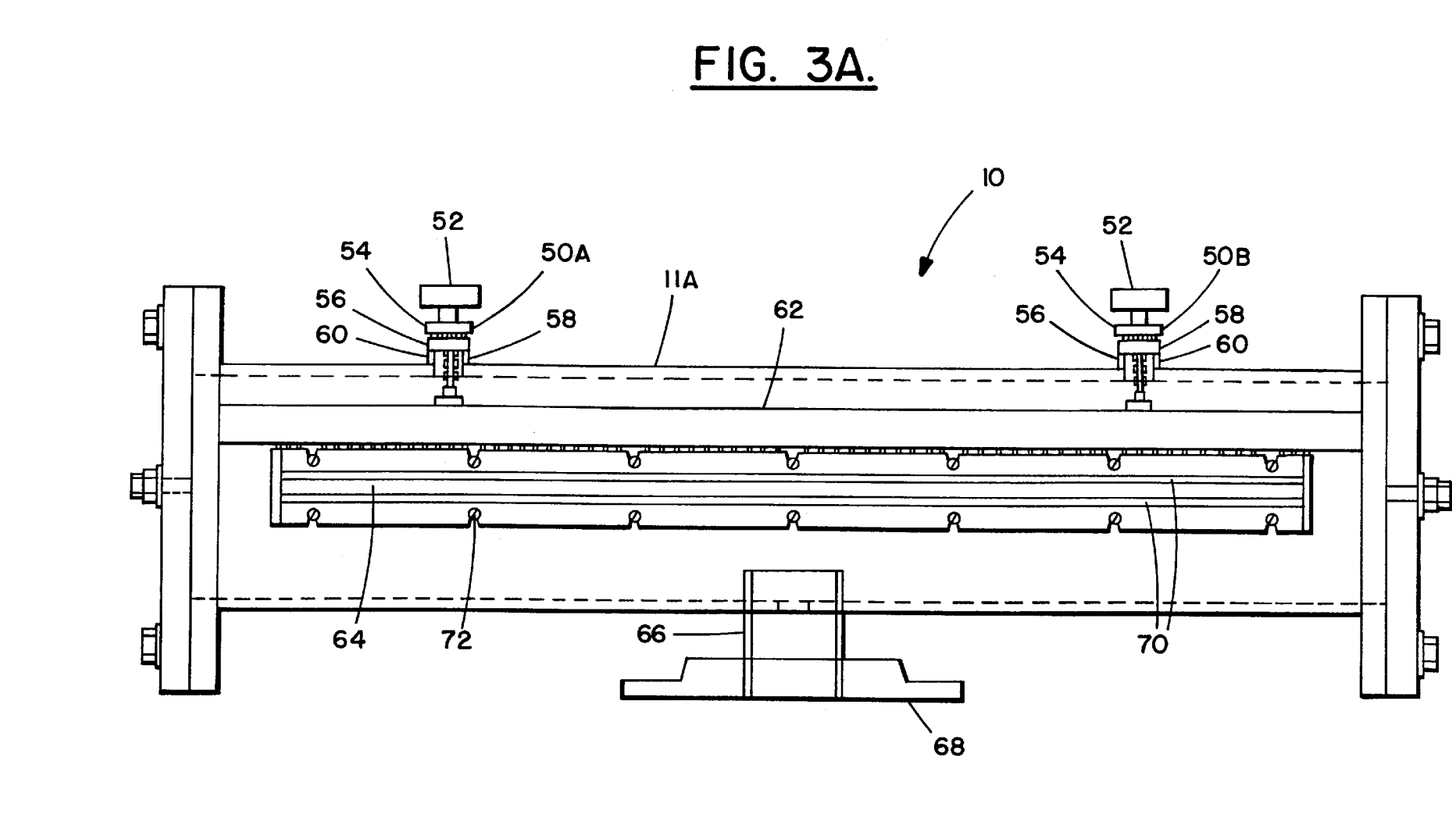
FIGS. 3A and 3B illustrate a second embodiment of a microwave applicator constructed in accordance with the present invention.
Figure 3B:
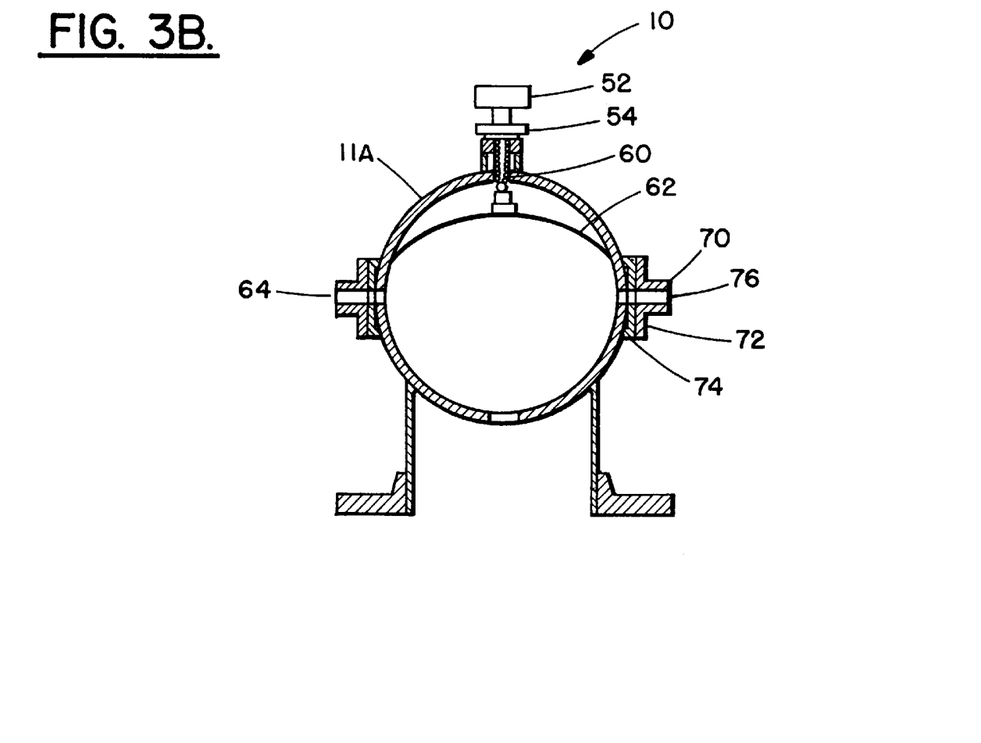

Referring to FIGS. 3A and 3B, a second embodiment of the invention provides an alternative approach for adjusting the cross-sectional area of an elongated chamber 11A, preferably having a cylindrical shape. Instead of separating the cylindrical chamber into two or more movable parts, the second embodiment includes a flexible metal foil 62 positioned inside the resonant cavity of cylindrical chamber 11A. Metal foil 62 is secured between the side walls of the resonant cavity and runs along the length of the cylinder such that it forms one portion or wall of the resonant cavity. As metal foil 62 is made of a flexible, conductive material (e.g., a beryllium/copper alloy or plated spring steel), the cross-sectional dimensions of the resonant cavity can be varied by simply applying an appropriate amount of pressure to metal foil 62, as shown in FIG. 3B. The greater the pressure, the more metal foil 62 reduces the cross-sectional diameter of the cavity of cylindrical chamber 11A. Conversely, the less the pressure, the greater the curvature of metal foil 62 and the larger the cross-sectional diameter of the cavity of cylindrical chamber 11A. As such, the cross-sectional shape of metal foil 62 can be adjusted to obtain a desired cavity diameter.

Referring to FIG. 3A, one mechanical method of applying pressure to metal foil 62 is shown. In particular, two adjustment mechanisms 50A, 50B enable a changing of the curvature of metal foil 62 and, thus, the cross-sectional diameter of the resonant cavity. Each adjustment mechanism 50A, 50B includes a head screw 52 having a threaded rod 60 coupled to metal foil 62, via tubular opening 56. The top planar surface of each tubular opening 56 has a cap 58 thereon with a threaded opening and a knurled check nut 58 for receiving threaded rod 60 therethrough. Knurled check nut 58 is positioned on the top of cap 58 to limit the range of motion of threaded rod 60. Accordingly, the diameter of the resonant cavity can be varied by rotating the head screws 52 in the appropriate direction and, thus, changing the cross-sectional shape of metal foil 62 to a desired curvature. The above operation may either be performed manually or in a fully automated fashion through computer control.

Note that while only two adjustment mechanisms 50A, 50B are illustrated in FIG. 3, applicator 10 may include any number of such adjustment devices. It is preferred that the adjustment mechanisms are evenly positioned along the length of the cylindrical applicator such that pressure can be applied uniformly across the flexible metal foil. The main reason is to ensure that the flexible metal foil maintains a uniform cross-sectional arcuate shape, e.g., curvature, along the length of the cylindrical applicator.

In order to process sheet-like material, cylindrical chamber 11A preferably includes two product openings 64 extending across the length of the cylinder and positioned on opposing sides of chamber 11A. The material to be processed is inserted through one opening and exits through the other opening. Each opening 64 is defined by a slot 76, an angle platform 74 and two L-shaped ridges 70 diametrically positioned above and below slot 76 of cylindrical chamber 11A. Angle platform 74 and L-shaped ridges extend along the length of opening 64 and are connected to cylindrical chamber 11A by screws 72. When connected, the above components form an upper and lower ridge having a space therebetween. The material to be processed can be inserted into and out of the cavity of cylindrical chamber 11A, via openings 64. It is important to understand that the extending ridges support the material as it is being processed and ensure that the material is fed into applicator 10 along a central horizontal axis.

The cylindrical chamber 11A may be an aluminum tube having a thickness of approximately 0.250 inches and a length of approximately 19.750 inches. Flexible metal foil 62 is metal plate preferably made of a beryllium/copper alloy and having a thickness of approximately 0.003 inches, a length of approximately 17.250 inches and a width of approximately 3.850 inches.

For both the first and second embodiments, microwave radiation can be coupled into applicator 10 using aniris, loop or antenna placed on the outer surface of the applicator or from the end of the applicator (e.g., end launch). The choice between the aforementioned devices depends on the material to be processed, the manner in which the dielectric properties change during processing and the resonant mode being utilized. Multiple launchers can also be used to improve uniformity and to generate higher power levels in the cavity.

Figure 4A:
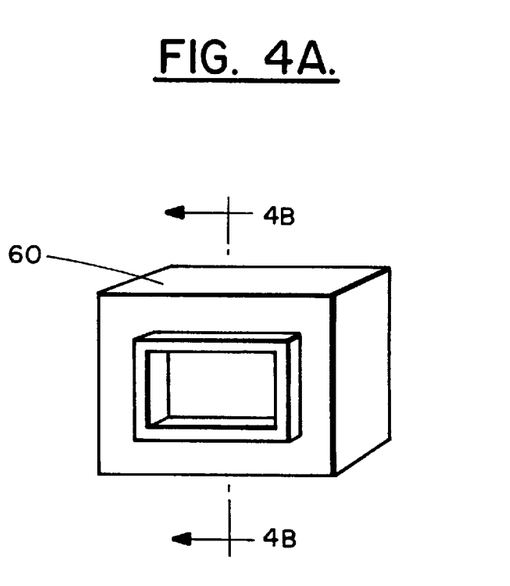
FIGS. 4A and 4B illustrates a top view and cross-sectional view of a preferred aperture.
Figure 4B:
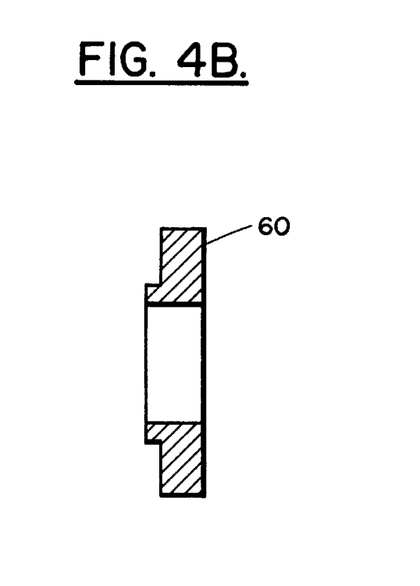
Figure 5:
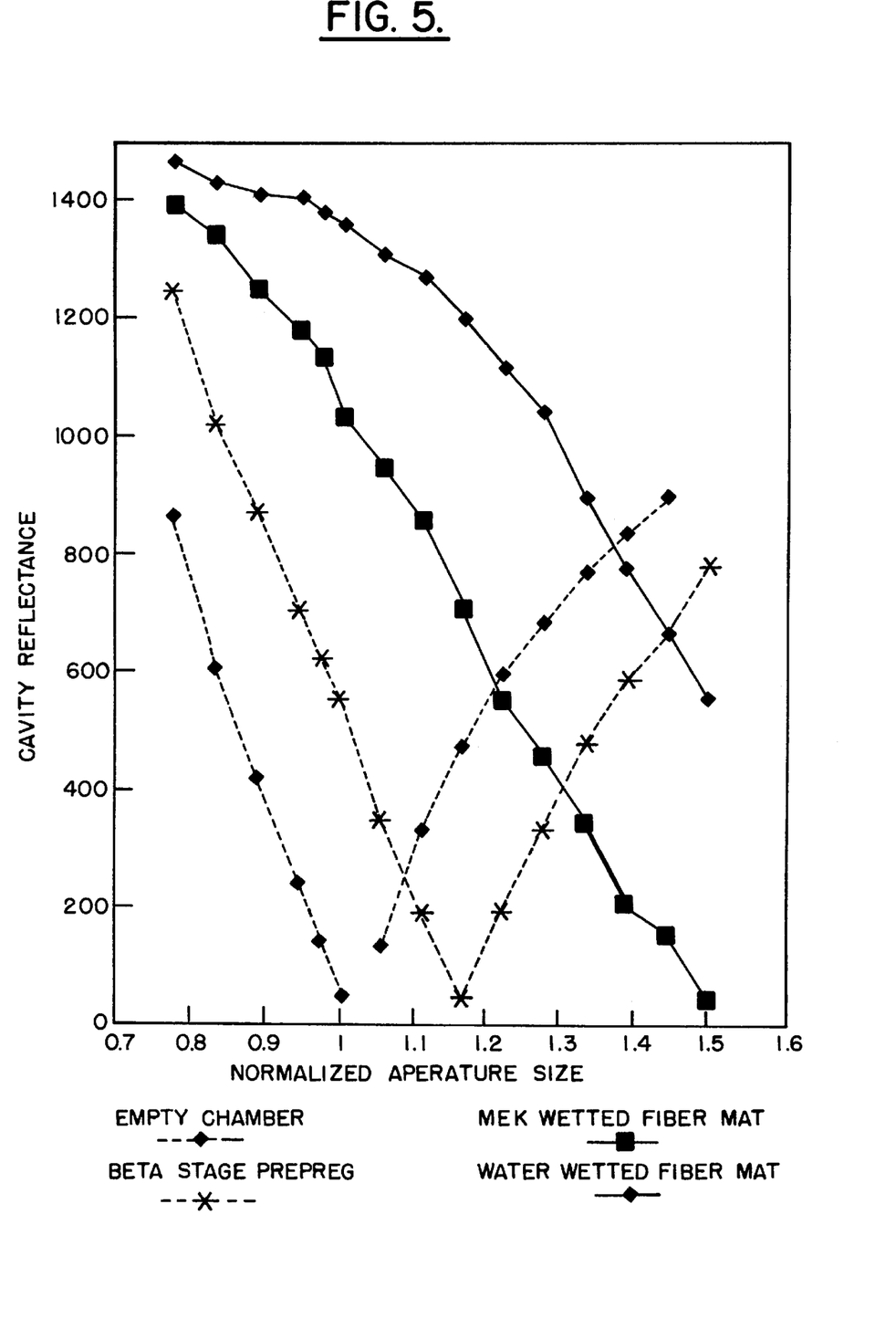
FIG. 5 illustrates a graph explaining the different loads affect on the optimum aperture size.

For cases in which a continuously moving web passes through applicator 10, the dielectric properties of the web reach a steady state after an initial period and change only minimally thereafter. In this case, provided that sufficient microwave energy can be coupled into microwave applicator 10 in the initial period to heat and process the web, only minimal variation in the coupling method is required to effectively match the impedance of applicator 10 and obtain substantially complete coupling of the microwave energy into the applicator. An iris or an aperture can be used such, as shown in FIGS. 4A and 4B. The size of the opening is selected before processing to account for a particular load and, thus, can not be varied during processing. The effect of different loads on the coupling efficiency and aperture size is shown in FIG. 5. A movable iris would also be used.

When the iris is placed on the outer wall of the applicator 10 and the fundamental mode of the launch waveguide is utilized, the length independent $TM_{0n0}$ modes are preferably selected. However, whenever there is a load in applicator 10 this provides a means for mode switching to other modes if the resonant frequency for that mode matches the microwave frequency. This problem is exacerbated as the length of the applicator is increased substantially since the normally length dependent modes can now be selected or sustained.

A continuously variable antenna can be used to couple microwave energy into the applicator in two modes, e.g., either through a sidewall launch if the TE modes are desired or through an end launch if the TM modes are desired to be excited. Such a device can be constructed in a similar manner to that of U.S. Pat. Nos. 4,507,588, 4,585,668, 4,630,566, 4,727,293, and U.S. Pat. No. 4,792,772 (Asmussen). Similarly, a coupling loop (e.g., a magnetic loop) can be utilized in either an end-launch configuration if the TE modes are desired or a side launch configuration if the TM modes are desired.

In the operation of the invention, when a material load is placed in the empty resonant cavity of the applicator 10, each electromagnetic resonance is shifted down in frequency and Q is lowered. The presence of the material load adds an additional material conductance and susceptance to the circuit. These additional circuit elements are functions of the material load placement, volume, shape and material properties.

The material load is irradiated with microwave energy by first adjusting the cross-sectional diameter of the cavity of applicator 10, as described above for the first and second embodiments. The specific resonant mode chosen depends on the shape and location of the material load. Once adjusted for a match in a pre-specified mode, preferably the length independent mode $TM_{010}$, microwave power is then applied and absorbed into the resonant cavity without reflection; and heating of the material then begins. As the material is heated, the material properties are altered, thereby resulting in a shift in the cavity resonance and a change in the input impedance of the applicator. In order to compensate for the changing material properties (e.g., the dielectric constant) during processing, the cross-sectional diameter of the applicator is varied iteratively until reflected power is reduced to zero, e.g., the applicator is matched as the material properties change. The tuning process can be quickly performed either manually or automatically by computer control as described above.

In addition to resonant mode selection and matching, the mechanical tuning feature of the present invention serves other practical functions as described below. For instance, it allows different material loads to be matched to a given constant frequency power source. Variations in the cavity resonant frequency caused by (1) the cavity expansion or contraction due to ambient temperature changes and (2) relative humidity changes in the air inside the resonant cavity can also be cancelled. Frequency drifts caused by variations in output power and heating of a power oscillator can be compensated for by mechanical tuning. Finally, it allows the applicator to be used with power oscillators which oscillate at different frequencies.

In summary, the applicator of the present invention can be utilized for a large range of materials processing applications, including solid materials processing and plasma processing in addition to the continuous processing of sheet. As described above, a complete series of modes can be achieved by varying the diameter of the applicator, and some may be more advantageous for a particular process. For example, the processing of silicon wafers using microwave energy has been found to be most effective utilizing the $TE_{111}$, $TM_{011}$ and has been theorized for the $TM_{010}$ modes to provide maximum uniformity over the workpiece. The latter cannot normally be selected since the dielectric properties change substantially during heating and processing, and hence a variable diameter applicator is the only method by which it can be selected and maintained during processing.

The invention having thus been described with particular reference to the preferred forms thereof, it will be obvious that various changes and modifications may be made therein without departing from the spirit and scope of the invention as defined in the appended claims.

We claim:

1. An apparatus for applying microwave energy having a substantially uniform field distribution over a large area for processing a material, said apparatus comprising:
   an elongated chamber having adjustment means for adjusting a cross-sectional area of said elongated chamber to control uniformity and mode of microwave energy therein during processing of said material; and
   means for coupling microwave power into said elongated chamber.

2. An apparatus as recited in claim 1, wherein said elongated chamber is separated into two halves along a length of said elongated chamber.

3. An apparatus as recited in claim 2, wherein said adjustment means changes the cross-sectional area of said elongated chamber by moving said halves towards and away from each other.

4. An apparatus as recited in claim 2, wherein said elongated chamber includes a space between and along the length of said two halves for allowing a sheet of material to pass therethrough.

5. An apparatus as recited in claim 1, wherein said elongated chamber is separated into at least two parts along a length of said elongated chamber.

6. An apparatus as recited in claim 5, wherein said adjustment means changes the cross-sectional area of said elongated chamber by moving said at least two parts towards and away from each other.

7. An apparatus as recited in claim 1, wherein said adjustment means includes a metal foil positioned between interior sidewalls of said elongated chamber and extending along a length of said elongated chamber.

8. An apparatus as recited in claim 7, wherein said metal foil exhibits a cross-sectional area within said elongated chamber and said adjustment means changes a cross-sectional area of said elongated chamber by changing dimensions of the cross-sectional area of said metal foil.

9. An apparatus as recited in claim 1, wherein said elongated chamber operates in a length independent mode.

10. An apparatus as recited in claim 1, wherein said elongated chamber operates in a $TM_{0Y0}$ mode.

11. An apparatus as recited in claim 1, wherein microwave energy having a substantially uniform electric field pattern is applied across the length of said elongated chamber.

12. An apparatus as recited in claim 1, wherein said elongated chamber includes an entrance opening and exit opening for allowing a sheet of material to pass through a center region of said elongated chamber.

13. An apparatus as recited in claim 1, wherein said large area extends substantially over the width of a sheet of material passing through said elongated chamber.

14. An apparatus as recited in claim 1, wherein said elongated chamber has an approximately circular cross-section.

15. An apparatus as recited in claim 14 wherein said elongated chamber comprises two cylindrical halves.

16. An apparatus as recited in claim 15, wherein said adjustment means changes the cross-sectional diameter of said elongated chamber by moving said cylindrical halves towards and away from each other.

17. An apparatus as recited in claim 15, wherein said elongated chamber includes a space between and along the length of said two cylindrical halves for allowing a sheet of material to pass therethrough.

18. An apparatus as recited in claim 14, wherein said elongated chamber is separated into at least two parts along a length of said elongated chamber.

19. An apparatus as recited in claim 1, wherein said elongated chamber has an approximately square cross-section.

20. An apparatus as recited in claim 1, wherein said elongated chamber has an approximately rectangular cross-section.

* * * * *